US010631722B2

(12) United States Patent
Asaoka et al.

(10) Patent No.: US 10,631,722 B2
(45) Date of Patent: Apr. 28, 2020

(54) VISUAL FIELD TESTING DEVICE

(71) Applicant: THE UNIVERSITY OF TOKYO, Tokyo (JP)

(72) Inventors: Ryo Asaoka, Tokyo (JP); Hiroshi Murata, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 156 days.

(21) Appl. No.: 15/577,315

(22) PCT Filed: May 18, 2016

(86) PCT No.: PCT/JP2016/064780
§ 371 (c)(1),
(2) Date: Nov. 27, 2017

(87) PCT Pub. No.: WO2016/190200
PCT Pub. Date: Dec. 1, 2016

(65) Prior Publication Data
US 2018/0153393 A1 Jun. 7, 2018

(30) Foreign Application Priority Data
May 28, 2015 (JP) .................. 2015-108950

(51) Int. Cl.
A61B 3/10 (2006.01)
A61B 3/02 (2006.01)
(Continued)

(52) U.S. Cl.
CPC ............ *A61B 3/024* (2013.01); *A61B 3/0025* (2013.01); *A61B 3/0041* (2013.01); *A61B 3/032* (2013.01);
(Continued)

(58) Field of Classification Search
CPC ......... A61B 3/024; A61B 3/113; A61B 3/102; A61B 5/0066; A61B 3/028; A61B 3/085;
(Continued)

(56) References Cited

U.S. PATENT DOCUMENTS 6,527,391 B1 3/2003 Heiji et al.
2005/0122476 A1 6/2005 Suzuki
(Continued)

FOREIGN PATENT DOCUMENTS

EP 1139855 A1 10/2001
JP 2005-102947 A 4/2005
(Continued)

OTHER PUBLICATIONS

International Search Report for PCT/JP2016/064780, dated Aug. 16, 2016.
(Continued)

*Primary Examiner* — Brandi N Thomas

(57) ABSTRACT

A probability distribution of visual sensitivities at each visual target presentation position of the subject is inferred on the basis of the test result information which is visual sensitivity information at each of the visual target presentation positions obtained through the tests performed in the past. Input of visual sensitivity information of the subject at at least one presentation position among the plurality of visual target presentation positions is received. Mutual information between visual sensitivity information of the subject regarding the visual test target represented by the received information and visual sensitivity information regarding each visual test target for which no visual sensitivity information of subject has been input, using the inferred probability distribution, is calculated, and the calculated mutual
(Continued)

information is provided for a predetermined process for selecting a position at which the next visual test target is to be presented.

3 Claims, 5 Drawing Sheets

(51) Int. Cl.
*A61B 3/024* (2006.01)
*A61B 3/032* (2006.01)
*A61B 3/036* (2006.01)
*A61B 3/00* (2006.01)
*G16H 50/20* (2018.01)
*A61B 3/06* (2006.01)

(52) U.S. Cl.
CPC .............. *A61B 3/036* (2013.01); *A61B 3/063* (2013.01); *G16H 50/20* (2018.01); *A61B 3/0091* (2013.01)

(58) Field of Classification Search
CPC ..... A61B 3/12; A61B 3/14; A61B 2562/0204; A61B 2562/0247; A61B 3/10; A61B 5/6803; A61B 3/08; A61B 2562/0219; A61B 3/0008; A61B 3/063; A61B 3/022; A61B 3/066; A61B 3/1015; A61B 3/1035; A61B 3/1216; A61B 3/13; A61B 3/165; A61B 5/0059; A61B 5/0077; A61B 5/01; A61B 5/0476; A61B 5/0496; A61B 5/14532; A61B 5/1455; A61B 5/14555
USPC ........ 351/200, 205–206, 209–211, 221–223, 351/243–246
See application file for complete search history.

(56) References Cited

U.S. PATENT DOCUMENTS

2010/0149488 A1* 6/2010 Lo .................. A61B 3/024 351/206
2016/0015263 A1 1/2016 Asaoka et al.
2017/0258316 A1 9/2017 Benner et al.

FOREIGN PATENT DOCUMENTS

| JP | 2015-142768 A | 8/2015 |
| WO | 2014/132470 A1 | 9/2014 |
| WO | 2015/027225 A1 | 2/2015 |

OTHER PUBLICATIONS

Written Opinion of the International Searching Authority for PCT/JP2016/064780, dated Aug. 16, 2016.
European Patent Office, Extended European Search Report (including Supplementary European Search Report) for European Patent Application No. 16799906.9, dated Mar. 8, 2019.

* cited by examiner

VISUAL FIELD TESTING DEVICE

TECHNICAL FIELD

The present disclosure relates to a visual-field test apparatus.

BACKGROUND ART

As a visual-field test apparatus for testing a visual field of a human, for example, Humphrey visual field analyzer is known. This visual field analyzer presents a visual target at one of a plurality of predetermined points located on a spherical visual field dome. A subject holds fixation on a fixation visual target located at a predetermined position, and when the subject can see the presented visual target, the subject presses a response switch. The visual target is, for example, a light spot projected at a point on the visual field dome. While the luminance and the presentation position of the light spot are changed, whether or not the subject presses the response switch is examined. Thereby, the visual field, and the visual sensitivity (referred to as a threshold) at a specific position of the visual field of the subject can be tested.

According to a conventional visual-field test apparatus, the position where a visual target is to be presented is determined by, for example, presenting a visual target at a predetermined position, examining whether the visual target presented at the position is visible or not, and thereafter, presenting a visual target at a visual target presentation position which is adjacent to the predetermined position and is closer to the fixation visual target, and so on. That is, visual targets are sequentially presented while the presentation positions are changed from the outer side of the visual field toward the fixation visual target.

According to a strategy for a threshold test, a luminance at a visual target presentation position is reduced in stages from a visible luminance to an invisible luminance, by a drop of 4 dB each time, and then, is raised in stages from the invisible luminance, by an increase of 2 dB each time, to thereby find a threshold. The same process is repeated at another visual target presentation position for the next threshold test.

Further, Japanese Unexamined Patent Publication (Kokai) No. 2005-102947 discloses a visual-field test apparatus for obtaining an evaluation value on the basis of responses of a subject, using a probability function, in order to obtain an objective evaluation value.

SUMMERY

Problem to be Solved by the Disclosure

However, according to the conventional visual-field test apparatus mentioned above, presenting visual targets at a large number of visual target presentation positions is required for obtaining an overall situation of a subject's visual field, resulting in requiring a long time.

In view of the above drawbacks, one of the objectives of the present disclosure is providing a visual-field test apparatus capable of reducing test time.

Solving Means

In order to solve the above drawbacks, the present disclosure provides a visual-field test apparatus which selects a visual test target position at which a visual test target is to be presented, from a plurality of visual target presentation positions, and presents, to a tester, a visual test target at the selected position, comprising: a holding device which holds visual sensitivity information at each of the visual target presentation positions obtained through the tests performed in the past, as test result information; an inference device which infers probability distribution of visual sensitivities at each visual target presentation position of the subject on the basis of the test result information held in the holding device; a reception device which receives input of visual sensitivity information of the subject at at least one presentation position among the plurality of visual target presentation positions; and a processing device which calculates mutual information between visual sensitivity information of the subject regarding the visual test target represented by the received information and visual sensitivity information regarding each visual test target for which no visual sensitivity information of subject has been input, using the inferred probability distribution, and provides the mutual information for a predetermined process for selecting a position at which the next visual test target is to be presented.

EMBODIMENT

Figure 1:
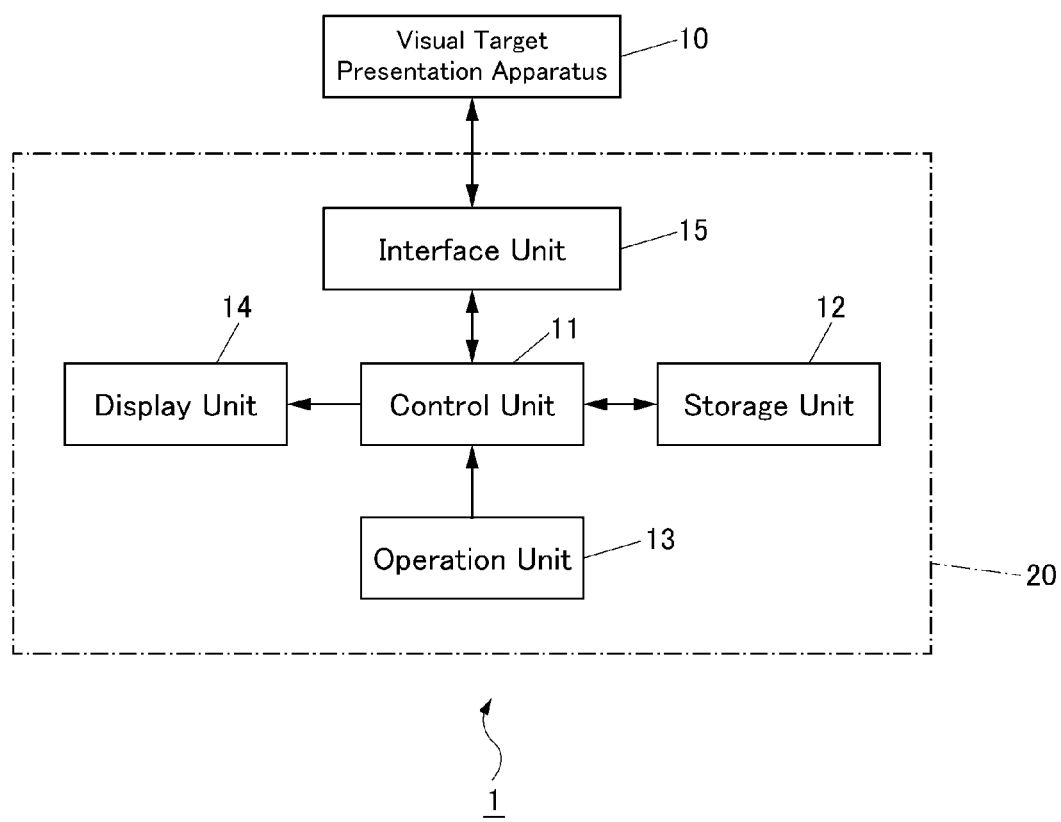
FIG. 1 is a block diagram showing a constitutional example of a visual-field test apparatus according to an embodiment of the present disclosure.

An embodiment of the present disclosure will be explained with reference to the drawings. As shown in FIG. 1, a visual-field test apparatus 1 according to the present embodiment comprises a visual target presentation apparatus 10, and a control apparatus 20. Here, the visual target presentation apparatus 10 presents a visual field dome and a visual test target to a subject, the visual test target being selected from a plurality of predetermined visual test targets on the visual field dome in response to an instruction input from the control apparatus 20, and being presented at a brightness defined by an instruction input from the control apparatus 20. As the visual target presentation apparatus 10, a widely known apparatus, etc., can be used for dimming a light from a light source to a designated brightness and projecting the light at a designated visual test target position on the visual field dome. Thus, a detailed explanation on the visual target presentation apparatus 10 is omitted here. The visual target presentation apparatus 10 is provided with a button (not shown) operated by a subject, and when the subject presses the button, information expressing that the button is pressed, is output.

As shown in FIG. 1, the control apparatus 20 comprises a control unit 11, a storage unit 12, an operation unit 13, a display unit 14, and an interface unit 15. The control unit 11 is an program controlled device such as a CPU, and operates in accordance with a program stored in the storage unit 12.

According to the present embodiment, the control unit 11 receives, from a user (tester), designation of a position (visual target presentation position) at which a visual test target is to be presented, and designation of a brightness of the visual test target to be presented at the position, and instructs the visual target presentation apparatus 10 to present the visual test target at the designated position and at the designated brightness. Then, upon receiving an input of a visual sensitivity of the subject at the visual target presentation position, the control unit 11 associates information which specifies the visual target presentation position with information which represents the input visual sensitivity (the darkest visible brightness, i.e., information representing threshold), and records the associated information in the storage unit 12 as a test record.

Further, the control unit 11 obtains at least a part of visual sensitivity information, at each visual target presentation position, of the past tests, as test result information, and infers a probability distribution of visual sensitivities of the subject, at each visual target presentation position, which represents a result of the visual field test. Using the inferred probability distribution, the control unit 11 calculates mutual information between the visual sensitivity information of the subject at at least one visual target presentation position which has been recorded in the storage unit 12 as a test record, and the visual sensitivity information of the subject at each visual target presentation position which has not been recorded as a test record (a position at which no visual sensitivity information of the subject has been recorded); and selects a visual target presentation position at which the mutual information satisfies a predetermined condition, as a subsequent presentation position. The control unit 11 presents, to the tester, information representing the selected visual target presentation position, by displaying the information on the display unit 14.

Further, upon receiving designation of a visual target presentation position at which a visual test target is to be presented, the control unit 11 may infer a brightness threshold of the subject at the visual target presentation position, and control the brightness of the visual test target to be presented at the visual target presentation position. Here, the inference is performed on the basis of the visibility probability for the brightness obtained from the test result information stored in the test result information database or obtained from the visual sensitivity information of the subject recorded in the test record, and an assumed visibility probability which has been previously assumed for a predetermined brightness. Detailed operations of the control unit 11 according to the present embodiment will be described later.

According to the present embodiment, upon receiving an instruction indicating the end of the test, the control unit 11 associates the test record recorded in the storage unit 12, with information specifying the subject (the information has already been input) and time and date of the test (such as year/month/date information obtained from a calendar IC (not shown)), and stores the resultant information in the test result information database in the storage unit 12.

The storage unit 12 is a memory device, a disk device, or the like, and stores a program which is executed by the control unit 11. The program may be provided while being stored in a computer-readable non-transitory storage medium, and stored in the storage unit 12. Also, the program may be delivered through a network, etc., and stored in the storage unit 12. The storage unit 12 also functions as a work memory of the control unit 11.

Figure 2:
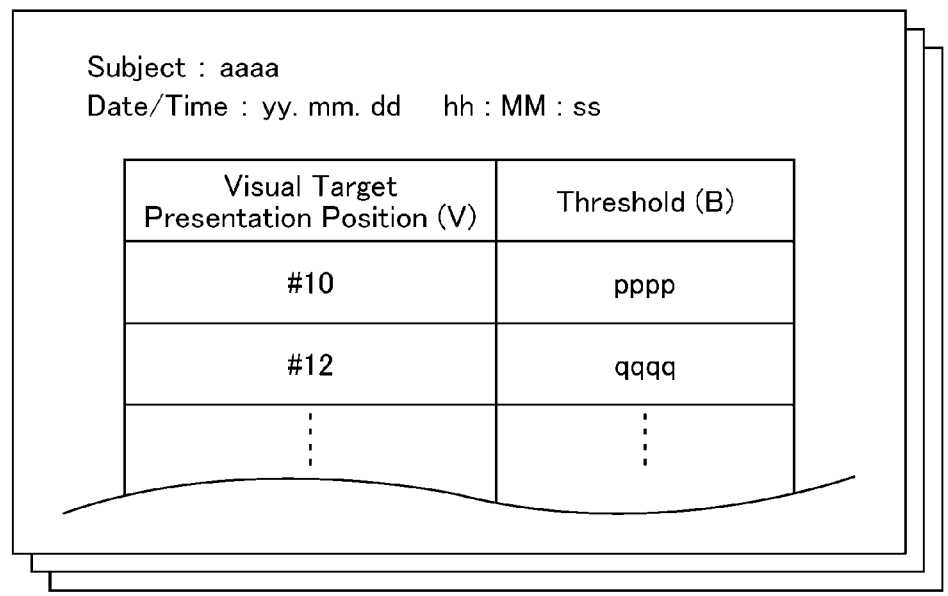
FIG. 2 is an explanatory view showing an example of a content of test result information to be used by a visual-field test apparatus according to an embodiment of the present disclosure.
Figure 3:
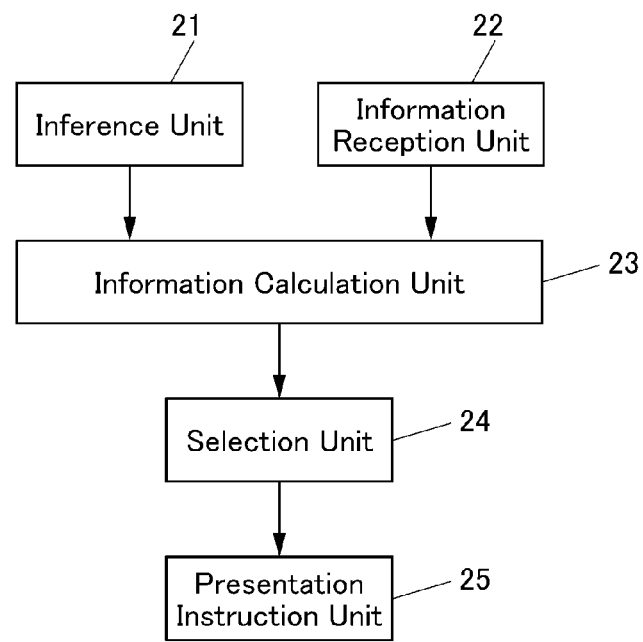
FIG. 3 is a functional block diagram showing an example of a control apparatus according to an embodiment of the present disclosure.

Further, according to the present embodiment, the storage unit 12 stores a test result information database, in which visual sensitivity information at at least a part of a plurality predetermined visual target presentation positions, obtained through the past tests, is accumulated. Specifically, the test result information database includes, as exemplified in FIG. 2, at least one piece of test result information representing the lowest visible brightness value (B) of the subject at each visual target presentation position (V), recorded in association with the subject specifying information (S) and the test date/time (D). According to the present embodiment, the test result information database is stored in the storage unit 12. However, the test result information database may be stored in a server, etc., connected through a network, and in accordance with needs, copied to the storage unit 12 to be used for the process. The storage unit 12 which (at least temporarily) stores the test result information database, corresponds to the holding device of the present disclosure.

The operation unit 13 is a mouse, a keyboard, etc., which receives operations by a tester who performs a test, and outputs instructions represented by the operations to the control unit 11. The display unit 14 is a display, etc., which displays information in accordance with the instructions input from the control unit 11. The display unit 14 presents information mainly to the tester.

The interface unit 15 is connected to the visual target presentation apparatus 10, and outputs instructions input from the control unit 11 to the visual target presentation apparatus 10. In addition, upon receiving an input of a signal representing that a button is pressed, from the visual target presentation apparatus 10, the interface unit 15 outputs the signal representing that a button is pressed, to the control unit 11.

Here, operations of the control unit 11 are to be explained. By executing the program stored in the storage unit 12, the control unit 11 of the present embodiment functionally comprises an inference unit 21, an information reception unit 22, an information calculation unit 23, a selection unit 24, and a presentation instruction unit 25, as exemplified in FIG.

The inference unit 21 infers a probability distribution of visual sensitivities of a subject at each visual target presentation position, on the basis of the past test result information accumulated in the test result information database. Here, the inference unit 21 may receive an input of information specifying a subject who is going to undergo the test, extract test result information of the subject specified by the information, and infer a probability distribution of visual sensitivities of the subject at each visual target presentation position on the basis of the extracted past test result information of the subject. If no past test result information is available for the subject who is going to undergo the test, or the available number of pieces of information is fewer than a predetermined threshold, the probability distribution of visual sensitivities of the subject at each visual target presentation position may be inferred on the basis of the test result information of any selected subject accumulated in the test result information database.

Further, any inference method may be applied for the inference of the probability distribution of visual sensitivities of a subject at each visual target presentation position, by the inference unit 21. Specifically, a method by Bayesian Inference, disclosed in WO/2014/132470 "Visual Field Test Assistance Apparatus", and the like, may be applied. Since WO/2014/132470 describes the method in detail, explanation therefor is not repeated here.

The information reception unit 22 receives an input of visual sensitivity information (the darkest visible brightness, i.e., information indicating threshold) of the subject at at least one visual target presentation position in a plurality of visual target presentation positions, associates information specifying the visual target presentation position with the input information representing the visual sensitivity, and records the resultant information in the storage unit 12 as a test record.

Using the probability distribution inferred by the inference unit 21, the information calculation unit 23 calculates mutual information between the visual sensitivity information of the subject at the visual target presentation position represented by the test record recorded in the storage unit 12, and the visual sensitivity information at each visual target presentation position which has not been recorded in the test record of the subject. Specifically, the information calculation unit 23 sequentially selects visual target presentation positions Wi(i=1, 2, . . . ) which have not been recorded in the test record of the subject, and obtains an uncertainty (information entropy) of the visual sensitivity information HWi(B) of the subject at each selected visual target presentation position Wi. The information entropy HWi(B) can be calculated by the following Formula (1), by referring to the probability distribution inferred by the inference unit 21, and using a probability pWi(Bj), each probability corresponding to each of a plurality of brightness candidates Bj(j=1, 2, . . . ) of the visual sensitivity information of the subject at the visual target presentation position Wi.

[Numerical Formula 1]

$$H_{Wi}(B) = -\sum_j p_{Wi}(B_j) \log(p_{Wi}(B_j)) \quad (1)$$

Further, the information calculation unit 23 refers to the test records recorded in the storage unit 12, and calculates an uncertainty (conditional information entropy) of the visual sensitivity information $H_v Wi(B)$ of the subject at a selected visual target presentation position Wi, when the visual sensitivity information B(Vk) at the visual target presentation position Vk(k=1, 2, . . . ) recorded in the test record is known.

The conditional information entropy $H_v Wi(B)$ can be calculated as the following Formula (2), by referring to the probability distribution inferred by the inference unit 21, and using a probability pWi(B(Vk), Bj) and a probability p(Vk). The probability pWi(B(Vk), Bj) refers to a probability that the visual sensitivity information of the subject at the visual target presentation position Wi is Bj (where Bj is one of a plurality of brightness candidates Bj(j=1, 2, and the visual sensitivity information of the subject at the visual target presentation position Vk is B(Vk). The probability p(Vk) refers to a probability that the visual sensitivity information of the subject at the visual target presentation position Vk is B(Vk) in the probability distribution inferred by the inference unit 21.

[Numerical Formula 2]

$$H_V W_i(B) = -\sum_k \sum_j \frac{p_{Wi}(B(V_k), B_j)}{p(V_k)} \log \frac{p_{Wi}(B(V_k), B_j)}{p(V_k)} \quad (2)$$

On the basis of Formula (1) and Formula (2), the information calculation unit 23 obtains mutual information I between the visual sensitivity information B(Vk) of the subject at the visual target presentation position Vk at which the test has been actually performed and which is recorded in the test record, and the visual sensitivity information Wi(Bj) of the subject at another visual target presentation position Wi (which is not recorded in the test record), as the following Formula (3).

[Numerical Formula 3]

$$I(B(V_k), W_i(B)) = H_{W_i(B)} - H_V W_i(B) \quad (3)$$

According to the definition of the Kullback-Leibler divergence, the obtained value can be calculated as a Kullback-Leibler divergence with the probability distribution inferred by the inference unit 21, as represented in Formula 4 below. In Formula 4, the Kullback-Leibler divergence is represented by using the probability distribution P(B(Vk)) regarding the probabilities that the visual sensitivity information of the subject at the visual target presentation position Vk is B(Vk), the probability distribution P (Wi(B)) regarding the probabilities that the visual information of the subject at the visual target presentation position Wi is one of the brightness candidates Bj, and the probability distribution P(B(Vk), Wi(B)) regarding the probabilities that, when the visual sensitivity information at the visual target presentation position Vk(k=1, 2, . . . ) is B(Vk), the visual sensitivity information of the subject at the visual target presentation position Wi is one of the brightness candidates Bj.

[Numerical Formula 4]

$$I(B(V_k), W_i(B)) = D_{KL}(P(B(V_k), W_i(B)) \| P(B(V_k)) P(W_i(B))) \quad (4)$$

The information calculation unit 23 calculates mutual information between the visual sensitivity information of the subject at the visual target presentation position represented by the test record recorded in storage unit 12, and the visual sensitivity information at each visual target presentation position which has not been recorded in the test record of the subject, and stores the value of the mutual information at each visual target presentation position which has not been recorded in the test record of the subject in the storage unit 12.

The selection unit 24 refers to the value of the mutual information at each visual target presentation position which has not been recorded in the test record of the subject, stored in the storage unit 12, and selects a visual target presentation position corresponding to the visual sensitivity information with which the mutual information satisfies a predetermined condition, the selected position being a position at which the next visual test target is to be presented. Specifically, the mutual information is defined as the uncertainty regarding the visual sensitivity of the subject at each visual target presentation position which has not been recorded in the test record of the subject, if the test result (information in the middle of the test) presently available and included in the test record, cannot be obtained. In other words, the mutual information is defined as how much amount of information can be obtained by measuring the visual sensitivity of the subject at each visual target presentation position which has not been recorded in the test record of the subject, relative to the test result (information in the middle of the test) presently available and included in the test record. Accordingly, if the selection unit 24 selects a visual target presentation position capable of maximizing the mutual information (namely, minimizing the conditional entropy), new and the larger amount of information can be obtained.

Therefore, the selection unit 24 refers to the value of the mutual information at each visual target presentation position which has not recorded in the test record of the subject, stored in the storage unit 12, selects a visual target presentation position corresponding to the maximum mutual information as a position at which the next visual test target is to be presented, and outputs information specifying the selected visual target presentation position.

The selected visual target presentation position does not have to correspond to the maximum mutual information. The selection unit 24 may select a visual target presentation position where the amount of the mutual information is more than a predetermined threshold. The threshold may be previously determined, or determined on the basis of mutual information obtained by the information calculation unit 23, for example, by using the dispersion σ of the mutual information, such that a value which is larger than the average value by a predetermined number of times of the dispersion σ, is determined as a threshold. At this time, if there are a plurality of visual target presentation positions capable of satisfying the condition, the selection unit 24 may select one visual target presentation position at random, or present the plurality of visual target presentation positions to the user (tester) so that the tester may select one visual target presentation position from the plurality of visual target presentation positions satisfying the condition. In case of the latter, the selection unit 24 outputs information which specifies the visual target presentation position selected by the tester.

The presentation instruction unit 25 displays, on the display unit 14, information indicating that a visual test target is to be presented at a visual target presentation position specified by the information output from the selection unit 24, and asks for the tester to input the brightness for presentation. When the presentation brightness is input, the presentation instruction unit 25 accepts the input, and outputs the input brightness information and the information specifying the visual target presentation position input from the selection unit 24, to the visual target presentation apparatus 10.

[Example for Inferring a Brightness Threshold of a Visual Test Target to be Presented]

Further, the presentation instruction unit 25 may infer a brightness threshold of the subject at a visual target presentation position where a visual test target is to be presented, and present the inferred result to the tester by displaying the result on the display unit 14. According to an example of present embodiment, the inference is performed on the basis of the visibility probability of brightness obtained from the test result information stored in the test result information database or the visual sensitivity information of the subject recorded in the test record, and the assumed visibility probability which is previously assumed for a predetermined brightness.

Specifically, the presentation instruction unit 25 obtains the brightness threshold (the brightness where the visibility probability is equal to the invisibility probability, i.e., the visibility probability is 0.5) of the subject at the visual target presentation position where the visual test target is to be presented, by Logistic regression. Namely, in advance, the visibility probability p(b) is supposed to comply with a logistic curve represented by Formula (5) below.

[Numerical Formula 5]

$$p(b) = \frac{1}{1 + e^{-\alpha - \beta b}} \qquad (5)$$

The logit function represented by Formula (6) corresponds to this logistic curve.

[Numerical Formula 6]

$$\log\left[\frac{p(b)}{1 - p(b)}\right] = \alpha + \beta b \qquad (6)$$

The slope α and the intercept β of the linear equation in the right side of this logit function, are determined by a least-squares method using information of the visibility probability regarding the brightness obtained from the test result information stored in the test result information database or the visual sensitivity information at the visual target presentation position of the subject recorded in the test record, and the assumed visibility probability previously assumed for a predetermined brightness. One of the characteristic features of the present embodiment is that not only the test result information stored in the test result information database or the visual sensitivity information at the visual target presentation position of the subject recorded in the test record, but also the assumed visibility probability information previously assumed for a predetermined brightness, is used. Namely, here, calculation of the least-squares method is performed under the conditions that the visibility probability is set to 1.0 (always visible) for the brightness higher than a predetermined first threshold θ1 (the brightness may be the maximum presentable brightness (indicated as 100% in the drawings)), among the presentable brightnesses, or, instead thereof or in addition thereto, the visibility probability is set to 0 (always invisible) for the brightness lower than a predetermined second threshold θ2 (the brightness may be the minimum presentable brightness), among the presentable brightnesses.

As an example, the presentation instruction unit 25 examines whether or not a predetermined number or more pieces of the test result information of the subject (visual sensitivity information associated with subject specifying information) is included in the test result information stored in the test result information database. Here, if the predetermined number or more (for example, ten or more times in the past) pieces of the test result information of the subject are included in test result information, the presentation instruction unit 25 reads out the test result information of the subject from the test result information stored in the test result information database. Whereas, if no test result information of the subject is stored in the test result information, the presentation instruction unit 25 reads out the test result information stored in the test result information database.

The presentation instruction unit 25 refers to the read-out test result information, obtains visibility probability (obtained by dividing the number of records indicated as visible by the number of tests) for each brightness in the past, at the visual target presentation position specified by the information input from the selection unit 24, stores the brightness value in association with the corresponding visibility probability. Further, at least one brightness value higher than the predetermined first threshold θ1 (the brightness may be the maximum brightness that can be presented) is stored in association with visibility probability "1". In addition, at least one brightness value lower than the predetermined second threshold θ2 (the brightness may be the minimum brightness that can be presented) is stored in association with visibility probability "0".

Figure 4:
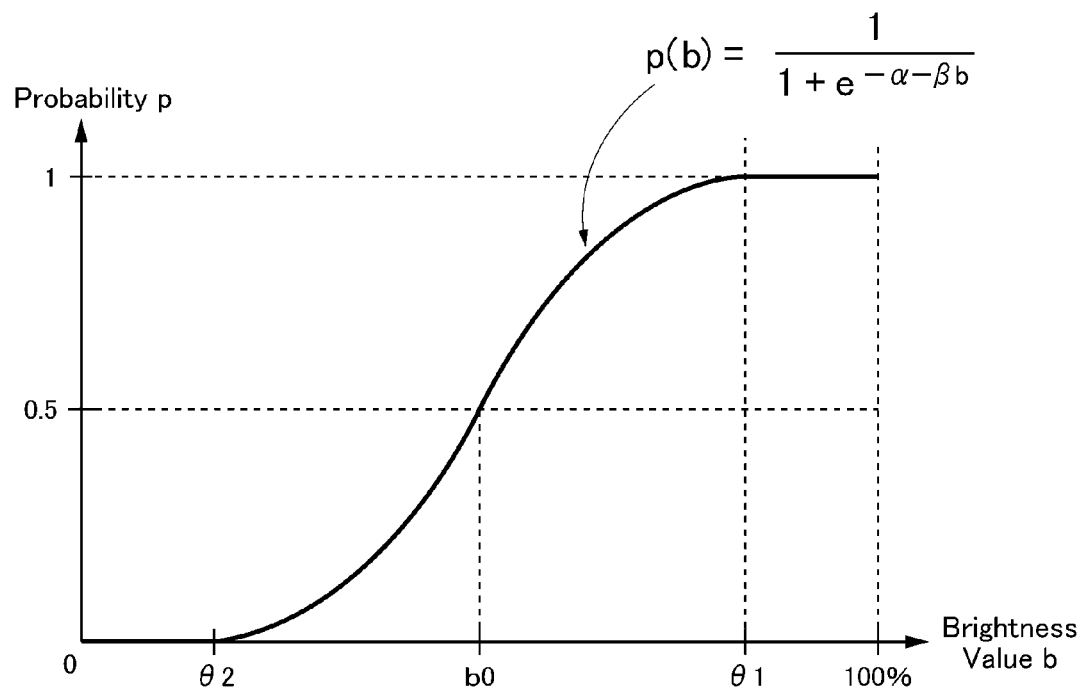
FIG. 4 is an explanatory view showing an example of a logistic curve calculated by a visual-field test apparatus according to an embodiment of the present disclosure.

The presentation instruction unit 25 plugs the brightness value and the visibility probability value which have been associated and stored, as sample data, into a logit function represented by Formula 6, and determines the slope α and the intercept β of the linear equation on the right side, by the least-squares method. Then, the presentation instruction unit 25 determines the logistic curve represented by Formula (5) (exemplified in FIG. 4) using the obtained a and and determines the brightness value b0 which corresponds to the visibility probability p(b)=0.5. Then, the presentation instruction unit 25 displays, on the display unit 14, the determined brightness value b0, together with information indicating that a visual test target is to be presented at the visual target presentation position specified by the information output from the selection unit 24, and prompts the tester to input a brightness for actual presentation. In this example, the tester refers to the presented brightness value b0 displayed by the presentation instruction unit 25, and instructs a brightness value to be actually presented.

Here, an example in which data is fitted to the logistic curve is explained. However, curve fitting may be performed for a probit curve or a log-log curve, and so forth. In any curve, fitting is performed so that the brightness having a higher brightness than a predetermined first threshold θ1 (the brightness may be the maximum brightness that can be presented)) corresponds to the visibility probability "1", and/or the brightness having a lower brightness than a predetermined second threshold θ2 (the brightness may be the minimum brightness that can be presented)) corresponds to the visibility probability "0".

Operations

Figure 5:
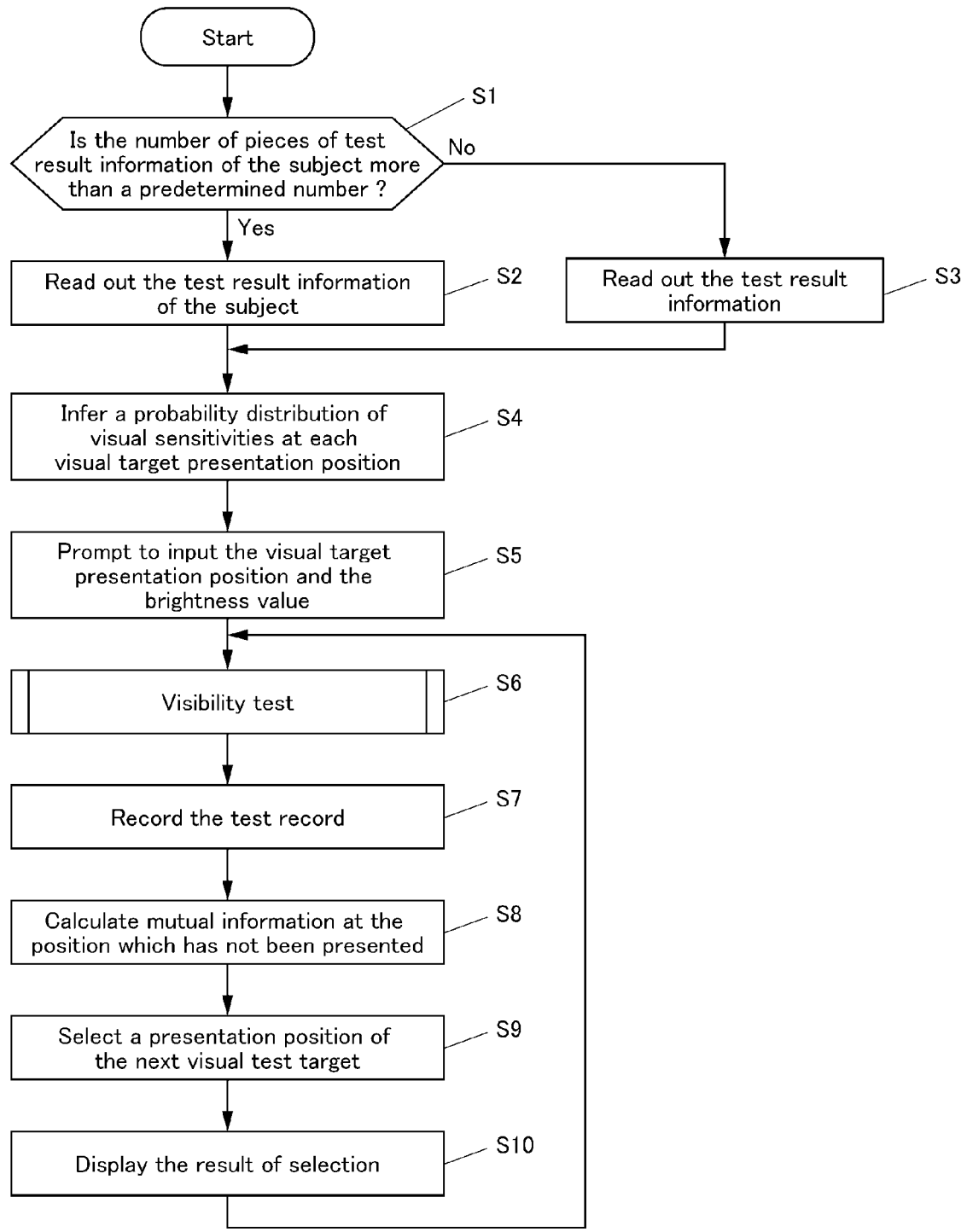
FIG. 5 is a flowchart showing an operation example of a visual-field test apparatus according to an embodiment of the present disclosure.

The visual-field test apparatus 1 according to the present embodiment is structured as above, and operates as below. First, a tester using the visual-field test apparatus 1 operates the control apparatus 20 to input information specifying the subject. The control apparatus 20 starts processes shown in FIG. 5, to store the subject specifying information which has been input, access the test result information database, and examine whether or not a predetermined number or more pieces of the test result information of the subject (visual sensitivity information associated with the subject specifying information) is included in the test result information of the past accumulated in the test result information database (S1).

Here, if the predetermined number or more (for example, the number is previously determined as ten or more times in the past) pieces of the test result information of the subject are included in the test result information (in case of Yes in S1), the control apparatus 20 reads out the test result information of the subject from the test result information stored in the test result information database (S2). Whereas, in S1, if the predetermined number or more pieces of the test result information of the subject are not included in the test result information (in case of No in S1), the control apparatus 20 reads out the test result information stored in the test result information database, regardless of whether the read-out test result information is that of the subject or not (S3).

After reading out the test result information in Step S2 or S3, the control apparatus 20 infers a probability distribution of visual sensitivities at each visual target presentation position of the subject, on the basis of the read-out test result information (S4). The method for inference used in Step S4 may be, for example, a method described in detail in WO/2014/132470 pamphlet.

The control apparatus 20 prompts the tester to input the first visual target presentation position and the brightness of the visual test target to be presented at the position (S5). In case that at least one visual target presentation position where the first visual test target is to be presented, is determined as default, the tester may be prompted to input only the brightness information of the visual test target, in this step. When the visual target presentation position and the brightness of the visual test target to be presented at the visual target presentation position are determined by the input information or by the previously determined information, the control apparatus 20 controls the visual target presentation apparatus 10 so that the visual test target having the determined brightness is presented at the determined visual target presentation position (S6: visibility test). Then, the visual target presentation apparatus 10 presents the visual test target having the determined brightness at the determined visual target presentation position. The subject presses the button of the visual target presentation apparatus 10 when the subject can visually recognize the visual test target.

In Step S6, the tester repeats inputting instructions for the brightness of the visual test target to be presented at the determined visual target presentation position, and the control apparatus 20 repeats controlling the visual target presentation apparatus 10 to present the visual test target having the instructed brightness at the visual target presentation position, until the lowest brightness value (or the invisibility of the target) of the subject at the visual target presentation position is found.

Thereby, the brightness value visible for the subject (threshold) at the determined visual target presentation position can be obtained. The control apparatus 20 associates the information specifying the visual target presentation position with the obtained threshold, and records the associated information as a test record (S7).

When the test record is obtained for at least one visual target presentation position, as mentioned above, the control apparatus 20 uses the inference probability distribution of Step 4, and calculates mutual information between the visual sensitivity information of the subject at the visual target presentation position represented by the test record recorded in Step S7 and the visual sensitivity information at each visual target presentation position which has not been recorded in the test record of the subject (S8).

The control apparatus 20 refers to the value of the mutual information regarding each visual target presentation position which has not been recorded in the test record of the subject, and selects a visual target presentation position corresponding to the visual sensitivity information with which the mutual information can satisfy a predetermined condition, as a visual target presentation position at which the next visual test target is to be presented (S9). Specifically, if the mutual information is defined as mentioned above, i.e., defined as information representing uncertainty of the visual sensitivity of the subject at each visual target presentation position which has not been recorded in the test record of the subject when the test record being obtained in the present test (information obtained by the middle of the test) and included in the test record is not obtained, which is, in other words, defined as information representing how much amount of the information becomes available when the visual sensitivity of the subject is measured at visual target presentation position which has not been recorded in the test record of the subject, relative to the test result being obtained in the present test (information obtained by the middle of the test) and included in the test record, the control apparatus 20 selects a visual target presentation position where the value of the mutual information becomes maximum. Then, the control apparatus 20 outputs information specifying the selected visual target presentation position, to the display unit 14 (S10). The tester refers to the display, and inputs a visual target presentation position at which the next visual test target is to be presented, as well as a brightness value of the visual test target to be presented. Upon receiving the input, the control apparatus 20 returns to Step S6, and proceeds to the subsequent steps.

According to an example of the present embodiment, when the tester instructs to terminate the test, the control apparatus 20 associates the recorded the test record with the subject specifying information and the test time/date information to generate test result information, and records the test result information in the test result information database.

Further, according to an example of the present embodiment, when the tester is prompted to input the brightness, the brightness threshold of the subject at the visual target presentation position where the visual test target is to be presented may be inferred by the test result information of the past, and regression analysis using the predetermined visibility probability value and the predetermined brightness corresponding thereto as sample data, and the inference result may be presented to the tester by displaying the result on the display unit 14. Here, for example, the brightness value which is visible at the ½ probability is inferred by the test result information in the past and Logistic regression using the predetermined visibility probability value and the predetermined brightness corresponding thereto as sample data, and the inference result is presented to the tester. The sample data of the predetermined brightness and the predetermined visibility probability may be the brightness higher than the predetermined first threshold (the brightness may be the maximum brightness which can be presented) among the brightness which can be presented and the corresponding visibility probability set to 1.0 (always visible), and the brightness lower than the predetermined second threshold (the brightness may be the minimum brightness which can be presented) among the brightness which can be presented and the corresponding visibility probability set to 0 (always invisible).

According to the above examples of the present embodiment, the position at which the visual test target should be presented can be guided by the mutual information, and the test time can be shortened.

Modified Example

According to the present embodiment, the visual target presentation position corresponding to the visual sensitivity information with which the mutual information can satisfy the predetermined condition is selected and presented as a position where the next visual test target is to be presented. However, the present disclosure is not limited thereto. For example, the control apparatus 20 of the present disclosure may obtain mutual information at respective visual target presentation positions which have not been recorded in the test record of the subject, and present, to the tester, a list of the mutual information at respective visual target presentation positions which have not been recorded in the test record of the subject, by displaying the list on the display unit 14.

The displayed list may be arranged as table view (in case of list is arranged as table view, the mutual information may be sorted in the ascending order or the descending order), or a figure schematically representing the visual field, the mutual information being displayed within the figure at a position corresponding to each visual target presentation position (the size of the mutual information may be expressed by numerical value, color, size of the figure, and the like).

Further, when the inference value of the brightness which is to be presented is also presented to the tester, as mentioned above, the inference value may be displayed together.

According to the present embodiment, a visual target presentation position at which a large amount of information can be obtained, is presented to the tester, and the tester can select the visual target presentation position on the basis of the information. Therefore, sufficient information regarding a visual field can be obtained through tests at a smaller number of visual target presentation positions. Thereby, the test time can be shortened.

Further, according to an example of the present embodiment in which the inference value of the brightness is also presented, the tester can refer to the relevant information, and set the brightness value of the visual test target to be presented to the subject. Thus, information regarding the threshold (the lowest visible brightness) of the subject can be obtained in fewer times, and thus, the test time can be shortened.

EXPLANATION ON NUMERALS 10 visual target presentation apparatus, 11 control unit, 12 storage unit, 13 operation unit, 14 display unit, 15 interface unit, 20 control apparatus, 21 inference unit, 22 information reception unit, 23 information calculation unit, 24 selection unit, 25 presentation instruction unit

The invention claimed is:

1. A visual-field test apparatus which selects a visual test target position at which a visual test target is to be presented, from a plurality of visual target presentation positions, and presents, to a tester, a visual test target at the selected position, on which a subject holds fixation, comprising:
  a holding device which holds visual sensitivity information at each of the visual target presentation positions obtained through the tests performed in the past in association with subject specifying information, as test result information;
  an inference device which infers probability distribution of visual sensitivities at each visual target presentation position of the subject such that, if a predetermined number or more pieces of the test result information of the subject are held in the holding device, the inference is performed on the basis of the test result information specified as information of the relevant subject by the subject specifying information, whereas, if not, the inference is performed on the basis of any test result information in the holding device regardless of whether the test result information is that of the relevant subject or not;
  a reception device which receives input of visual sensitivity information of the subject at at least one presentation position among the plurality of visual target presentation positions; and a processing device which calculates mutual information between visual sensitivity information of the subject regarding the visual test target represented by the received information and visual sensitivity information regarding each visual test target for which no visual sensitivity information of subject has been input, using the inferred probability distribution, and provides the mutual information for a predetermined process for selecting a position at which the next visual test target is to be presented.

2. A visual-field test apparatus according to claim 1, wherein, the processing device performs a process of selecting a visual target presentation position corresponding to visual sensitivity information with which the mutual information satisfies a predetermined condition, as a position at which the next visual test target is to be presented, and presenting a visual test target at the selected position.

3. A visual-field test apparatus according to claim 1, further comprising, an inference device which infers a brightness threshold of the subject at the visual target presentation position at which the visual test target is to be presented, and a brightness control device which controls the brightness of the visual test target to be presented, wherein the inference device infers a brightness threshold of the subject on the basis of a visibility probability at a brightness which is obtained from the test result information held in the holding device or the visual sensitivity information which has been input, and an assumed visibility probability which is previously assumed for a predetermined brightness.

* * * * *